US006998055B2

United States Patent
Tajima

(10) Patent No.: US 6,998,055 B2
(45) Date of Patent: Feb. 14, 2006

(54) CONCENTRATION DEVICE USING MAGNETIC PARTICLES AND METHOD THEREFOR

(75) Inventor: Hideji Tajima, Matsudo (JP)

(73) Assignee: Precision System Science Co., Ltd., Matsudo (JP)

(*) Notice: Subject to any disclaimer, the term of this patent is extended or adjusted under 35 U.S.C. 154(b) by 0 days.

(21) Appl. No.: 10/802,269

(22) Filed: Mar. 17, 2004

(65) Prior Publication Data
US 2004/0173537 A1    Sep. 9, 2004

Related U.S. Application Data

(62) Division of application No. 09/889,762, filed as application No. PCT/JP00/00204 on Jan. 18, 2000, now Pat. No. 6,723,237.

(30) Foreign Application Priority Data

Jan. 18, 1999   (JP)   ............................... 11-9672

(51) Int. Cl.
*B03C 1/00*   (2006.01)
*G01N 1/00*   (2006.01)
*G01N 33/53*  (2006.01)
*C12Q 1/68*   (2006.01)

(52) U.S. Cl. .................. 210/695; 210/222; 422/100; 422/101; 436/177; 436/526

(58) Field of Classification Search ............. 210/222, 210/695; 436/526, 177; 422/100, 101
See application file for complete search history.

(56) References Cited

U.S. PATENT DOCUMENTS

| 4,141,687 A | 2/1979 | Forrest et al. |
| 5,147,529 A | 9/1992 | Lee et al. |
| 5,895,631 A | 4/1999 | Tajima |
| 6,027,945 A * | 2/2000 | Smith et al. ............... 436/526 |

FOREIGN PATENT DOCUMENTS

| JP | 60-189834 | 12/1985 |
| JP | 10-332687 A | 12/1998 |
| WO | WO 96/29602 A1 | 9/1996 |
| WO | WO 9831840 A1 * | 7/1998 |

OTHER PUBLICATIONS

Translation of JP 10-332687 A which is published on Dec. 1998.*

* cited by examiner

*Primary Examiner*—David A. Reifsnyder
(74) *Attorney, Agent, or Firm*—Haynes and Boone, LLP

(57) ABSTRACT

The invention relates to a concentration device using magnetic particles and a method therefor aimed at performing concentration of a large volume of liquid efficiently and reliably with a simple structure and on a small device scale. The construction involves having: a liquid suction passage in which liquid can pass through only in a suction direction; a liquid discharge passage in which liquid can pass through only in a discharge direction; a magnetic force device which can exert a magnetic field from outside of the liquid passage on at least one liquid passage thereof or remove the magnetic field, and which can separate magnetic particles having directly or indirectly captured a target substance suspended in the liquid by having the magnetic particles adhere to the inner wall of the liquid passage; a storage section communicated with each liquid passage, for storing the sucked liquid; and a pressure adjustment device for sucking and discharging the liquid by adjusting the pressure in the storage section.

4 Claims, 4 Drawing Sheets

CONCENTRATION DEVICE USING MAGNETIC PARTICLES AND METHOD THEREFOR

CROSS-REFERENCE TO RELATED APPLICATIONS

This application is a divisional of prior application Ser. No. 09/889,762 filed Jan. 11, 2002, now U.S. Pat. No. 6,723,237, the entire disclosure of which is incorporated herein by reference, which is a U.S. national phase filing of International Application No. PCT/JP00/00204 filed Jan. 18, 2000, the entire disclosure of which is incorporated herein by reference, which claims priority from prior Japanese Application No. 11-9672 filed Jan. 18, 1999, the entire disclosure of which is incorporated herein by reference.

TECHNICAL FIELD

The present invention relates to a concentration device using magnetic particles and a method therefor. More particularly, the present invention relates to a concentration device using magnetic particles and a concentration method using magnetic particles applied to medical treatment, examination, diagnosis, treatment, research, quantitative, qualitative, measurement or the like, in which concentration is automatically and reliably increased so that a target substance such as a microscopic amount of bacteria to be suspended in a large volume of liquid, is concentrated to thereby be suspended in a small volume of liquid, in order to perform processing such as separation, extraction or recovery of, for example, immunity substances such as antibodies or antigens, genetic substances (DNA, RNA, mRNA, oligonucleotide or the like), biopolymers such as proteins or hormone substances, organisms such as bacteria, viruses, cells, or other useful compounds such as medical drugs, in various fields such as the engineering field, medical field, agricultural field, scientific field and pharmaceutical science field.

BACKGROUND ART

Recently, the need for performing various processing such as separation, extraction, inspection or measurement of target substances such as organisms or biopolymers of bacteria or the like (for example, aqueous dissolved bacteria such as O-157, *cryptolipolysium, salmonella* or the like, genetic materials such as DNA) is increasing.

For the purpose thereof, it is necessary to perform various processing after having cultured the bacteria, or in the case of genetic materials or the like, after having increased the concentration of the target substance by performing amplification.

The target substance such as bacteria or genetic materials is naturally obtained with a small amount thereof suspended in a large volume (for example, several liters) of liquid. In order to perform culture or amplification for this target substance, it is necessary to extract or separate the target substance from the suspension.

Therefore, separation and extraction has been heretofore performed by passing a large volume of suspension containing the target substance suspended therein through a filter. Normally, however, many impurities are contained other than the target substance in the suspension. In the case of a membrane filter or the like, these are likely to cause clogging due to the impurity and fouling. Hence this has the problem in that it is difficult or it requires time and labor to separate the target substance from a large volume of suspension.

Moreover, considering a case where a substance such as bacteria that affect organisms such as humans is handled, there is a demand for an apparatus which can automatically perform processing without requiring human intervention, which makes it possible to replace a part coming in contact with the suspension, and which does not require cleaning and can be used efficiently and reliably.

It is therefore a first object of the present invention to provide a concentration device using magnetic particles and a concentration method using magnetic particles, which can perform concentration of a large volume of liquid efficiently, quickly and reliably.

It is a second object of the present invention to provide a concentration device using magnetic particles and a concentration method using magnetic particles, wherein concentration, separation or extraction processing is not affected by the existence of impurities.

It is a third object of the present invention to provide a concentration device using magnetic particles and a concentration method using magnetic particles, wherein the part coming in contact with the suspension can have a construction such that a container or a disposable tip can be replaced, and a simple mechanism is used to thereby make it low-priced and easy to handle, without requiring cleaning.

It is a fourth object of the present invention to provide a concentration device using magnetic particles and a concentration method using magnetic particles, which are suitable for automated processing and consistent processing without requiring human intervention.

It is a fifth object of the present invention to provide a concentration device using magnetic particles and a concentration method using magnetic particles, suitable for handling microorganisms such as bacteria and biopolymers such as DNA substances. More particularly, it is an object of the present invention to provide a concentration device using magnetic particles and a concentration method using magnetic particles, suitable for amplification by a PCR method for genetic materials such as DNA.

DISCLOSURE OF THE INVENTION

In order to solve the above technical problems, a first aspect of the present invention is characterized by comprising: a liquid suction passage in which liquid can pass through only in a suction direction; a liquid discharge passage in which liquid can pass through only in a discharge direction; a magnetic force device which can exert a magnetic field from outside of the liquid passage on at least one liquid passage thereof or remove the magnetic field, and which can separate magnetic particles having directly or indirectly captured a target substance suspended in the liquid by having the magnetic particles adhere to the inner wall of the liquid passage; a storage section communicated with each liquid passage, for storing the sucked liquid; and a pressure adjustment device for sucking and discharging the liquid by adjusting the pressure in the storage section.

The term "directly capturing the target substance" herein stands for capturing the target substance by bonding the target substance such as bacteria with the magnetic particles. In order to do that, it is necessary that the magnetic particles have a substance for bonding with the target substance by means of a coating or the like. For example, there can be mentioned a case where glass is coated on the magnetic particles, and genetic materials such as DNA are adsorbed on the glass and captured.

The term "indirectly capturing the target substance" herein stands for a case where magnetic particles, target substance and a carrier originally existing separately and independently are suspended in liquid, and the carrier bonds with the magnetic particles and the target substance, so that magnetic particles capture the target substance. As the carrier, for example, there are gel substances such as hydroxyapatite and a cellulose carrier. When a gel substance such as hydroxyapatite is used as a carrier, the gel substance takes both the magnetic particles and the target substance into the inside thereof to thereby capture the target substance. When the cellulose carrier is used as a carrier, magnetic particles and the target substance are adhered to holes and gaps in the cellulose carrier to thereby capture the target substance. Capture can be effected by putting the magnetic particles or magnetic particles and the carrier into the liquid containing the target substance, and mixing or stirring these. The target substance captured by the magnetic particles can be dissolved by physical processing such as stirring or heating, or can be eluted or alienated from the magnetic particles by chemical processing such as by adjusting the pH to dissolve the target substance as with the hydroxyapatite, or by mixing with a reagent. The liquid suction passage and the liquid discharge passage are capable of passing the liquid only in the suction direction or in the discharge direction of the liquid by, for example, a check valve. The check valve may be provided in a part of the liquid suction passage and the liquid discharge passage, or may be provided outside the liquid suction passage and the liquid discharge passage, for example, attached to the storage section. When the suction port and the discharge port of the liquid passage are inserted into different containers, the suspension before separating the magnetic particles and the residual liquid after the separation thereof can be separated, thereby enabling efficiency improvement of the processing. When these ports are inserted into the same container, the liquid passage forms a circuit, thereby enabling separation to be repeated without replacing the suction port and the discharge port.

According to the first aspect, at the time of repeating a simple operation such as passing a large volume of suspension through the liquid passage, or sucking the liquid from the liquid suction passage and discharging the liquid from the liquid discharge passage, with respect to all of the suspension, the magnetic particles in the suspension are automatically separated. Hence, all of the magnetic particles in the suspension can be efficiently and easily separated with a simple construction and without leakage.

According to the present invention, by re-suspending the separated magnetic particles in an optional amount of liquid, concentration to an optional proportion can be performed. Hence, the culture process and the amplification process thereafter can be made efficient, and the density of a large volume of suspension in which the target substance is suspended in a dilute amount can be increased efficiently or within a short period of time.

According to the present invention, the target substance can be captured by magnetic particles, and the liquid can be made to pass through the liquid passage, with the magnetic particles attracted to the liquid passage and separated, by exerting a magnetic field from outside of the liquid passage. Hence, since impurities can be eliminated by the suction and discharge operation, separation, extraction or the like of the target substance is not hindered.

Also, in the case where the magnetic particles capture the target substance indirectly via a carrier, it is not necessary to perform processing such as coating with respect to the magnetic particles. Hence processing can be performed at a low cost.

A second aspect of the present invention is characterized in that in the first aspect, the liquid suction passage and the liquid discharge passage are provided in parallel to each other with a space, so as to protrude downward below the storage section, with the pressure adjustment device provided above the storage section. According to the present invention, since the liquid suction passage and the liquid discharge passage are provided in parallel to each other with a space, if a container that can be divided by that space is prepared and each liquid passage is inserted therein, the sucked liquid can be discharged to another container without requiring a shift. According to the second aspect, since the liquid suction passage and the liquid discharge passage are provided so as to protrude downward below the storage section, and the pressure adjustment device is provided above the storage section, the apparatus can be made compact, and concentration processing can be performed efficiently by using a special container.

A third aspect of the present invention is characterized in that in the first aspect or in the second aspect, the liquid suction passage and the liquid discharge passage are formed substantially in a two-stage form with a tip portion having a small diameter and a large-diameter portion, respectively. Hence the liquid passage can be inserted also with respect to a container having a thin opening, and by performing separation of the magnetic particles by the large-diameter portion, clogging or the like can be prevented. According to the third aspect, insertion is also possible with respect to a container having a thin opening, and clogging or the like can be prevented at the time of performing separation of magnetic particles.

A fourth aspect of the present invention is characterized in that in any one of the first aspect to the third aspect, the magnetic force device is obtained by providing a permanent magnet, an electromagnet or a magnetic substance outside of at least one of the liquid passages. In the case of the permanent magnet, by providing this so as to be able to be brought near or alienated from the liquid passage, the magnetic field can be exerted or removed.

Moreover, in the case of the electromagnet, by flowing or cutting off the electric current, the magnetic field is generated or removed. In the case of the magnetic substance, by magnetizing or demagnetizing the magnetic substance, the magnetic field is generated or removed. As a result, the magnetic field can be reliably exerted or removed. According to the fourth aspect, the magnetic field can be reliably exerted on or removed from the inside of the liquid passage.

A fifth aspect of the present invention is characterized in that in any one of the first aspect to the fourth aspect, the storage section has a cylinder, and the pressure adjustment device has a plunger inserted into the cylinder so as to slide therein. Here, in the storage section, it is desirable to control so that the surface of the sucked liquid and the bottom surface of the piston do not come in contact with each other via an air layer. As a result, contact between the mechanical part and the suspension can be avoided, thereby enabling reuse without requiring cleaning. Moreover, it is desirable to provide an O-ring groove around the circumference of the plunger, so as to attach an O-ring formed of a resilient body in that groove. As a result, liquid leakage can be reliably prevented. With the fifth aspect, by controlling so that the surface of the sucked liquid and the bottom surface of the piston do not come in contact with each other via the air layer, in the storage section, reliable processing can be performed without the possibility of contamination.

A sixth aspect of the present invention is characterized in that in any one of the first aspect to the fifth aspect, the pressure adjustment device has an air flow path provided in the storage section, and a pump for performing suction and discharge of a gas in the storage section via the air flow path. As a result, the structure thereof can be made simple and cleaning becomes easy, without requiring a complicated mechanical portion in the storage section. With the sixth aspect, the pressure adjustment device is communicated with the pump performing suction and discharge of a gas in the storage section, via the storage section and the air flow path. Hence, it is not required to provide a complicated mechanical portion in the storage section, thereby simplifying the structure and making cleaning easy.

A seventh aspect of the present invention is characterized in that in any one of the first aspect to the sixth aspect, the storage section is provided detachably with respect to the pressure adjustment device. Here, the liquid suction passage and the liquid discharge passage may be formed integrally with the storage section, or may be provided detachably with respect to the storage section. According to the present invention, since the storage section including the liquid suction passage and the liquid discharge passage is provided detachably with respect to the pressure adjustment device, by attaching a new storage section, processing can be proceeded without cleaning. Hence, rapid processing is possible. According to the seventh aspect, since the storage section is provided detachably with respect to the pressure adjustment device, by attaching a new storage section, processing can be proceeded without cleaning. As a result, this is very efficient.

An eighth aspect of the present invention is characterized in that in the seventh aspect, when the storage section is detached, the pressure adjustment device can be mounted with one pipette tip, in which the liquid can pass through both in the suction direction and the discharge direction. As a result, efficient processing is possible by using the same pressure adjustment device and replacing only a portion contacting with the suspension.

A ninth aspect of the present invention is characterized in that in any one of the first aspect to the eighth aspect, hydroxyapatite is sintered and secured to the magnetic particles, and the pH of the solution containing the magnetic particles suspended therein is adjusted to change the hydroxyapatite to a sol form or a gel form, to thereby make the hydroxyapatite capture or alienate the target substance. According to the present invention, by a simple operation such as adjustment of pH, the hydroxyapatite is changed to a gel form or a sol form so that the magnetic particles can capture the target substance, or the target substance can be eluted or alienated.

A tenth aspect of the present invention is characterized by comprising: a liquid passage having a suction port and a discharge port, in which liquid can pass therethrough; a magnetic force device which can exert a magnetic field from outside of the liquid passage, which can separate magnetic particles having directly or indirectly captured a target substance suspended in the liquid, by having the magnetic particles adhere to an inner wall of the liquid passage; and a pump provided in the liquid passage, for transferring the liquid along a transfer direction of the liquid in the liquid passage.

As a result, magnetic particles in the suspension can be separated or re-suspended during passing through the liquid passage without leakage, with a simple structure and a simple control.

As the "pump", for example, a peristaltic pump may be used, in which a part or the whole of the liquid passage is formed of a resilient body, and liquid is transferred by sequentially making the liquid passage contract from the outside along the transfer direction of the liquid.

At that time, since there is no contact between the suspension and the mechanical portion for transfer or the magnetic force device, the device can be reused by merely cleaning or replacing the liquid passage. Contact between the suspension containing the target substance such as bacteria suspended therein and the mechanical portion can be avoided or can be made minimum. Particularly, the resilient body portion may be cut and formed detachably, for example, by making as a cartridge. In such a case, this is taken out together with the magnetic particles attracted to that portion, to thereby perform processing such as re-suspension.

According to the tenth aspect, at the time of repeating a simple operation such as passing a large volume of suspension through the liquid passage, or sucking the liquid from the liquid suction passage and discharging the liquid from the liquid discharge passage, with respect to the whole suspension, the magnetic particles in the suspension are automatically separated. Hence, all of the magnetic particles in the suspension can be efficiently and easily separated with a simple construction and without leakage.

According to the present invention, by re-suspending the separated magnetic particles in an optional amount of liquid, concentration to an optional proportion can be performed.

Also, in the case where the magnetic particles capture the target substance indirectly via a carrier, it is not necessary to perform processing such as coating with respect to the magnetic particles. Hence processing can be performed at a low cost.

An eleventh aspect of the present invention is characterized in that in the tenth aspect, a switchover mechanism for switching over the liquid passage in order to re-suspend and discharge the separated magnetic particles is provided in the middle of the liquid passage. In order to switchover, for example, a rotor having a through hole is rotatably provided in the middle of the liquid passage, and at the time of separating the magnetic particles from the suspension, the rotation position of the rotor is set so as to communicate with the liquid passage, and at the time of re-suspension, the rotation position is set so that passing in both the suction direction and the discharge direction of the liquid is possible, and so as to communicate with another liquid passage (pipette device) having a magnetic force device capable of exerting a magnetic field therein. According to the eleventh aspect, by using a liquid passage for re-suspension which is different from the liquid passage for separation, separation and re-suspension can be effectively performed.

A twelfth aspect of the present invention is characterized in that in the tenth aspect or the eleventh aspect, a whole of the liquid passage or a part of the liquid passage is provided so as to be able to be taken out, while attracting the separated magnetic particles. As a construction capable of being taken out, for example, this may be taken out by removing a member attaching the whole liquid passage to a frame or the like, or only a part of the liquid passage may be provided detachably from other parts of the liquid passage. The removed part may be directly attached to an apparatus for performing processing and then used. According to the twelfth aspect, by taking out the whole or a part of the liquid passage, the separated magnetic particles can be used. Hence, processing such as concentration can be easily performed.

A thirteenth aspect of the present invention is characterized in that in the tenth aspect to the twelfth aspect, hydroxyapatite is sintered and secured to the magnetic particles, and the pH of the solution containing the magnetic particles suspended therein is adjusted to change the hydroxyapatite to a sol form or a gel form, to thereby make the hydroxyapatite capture or alienate the target substance. According to the present invention, by a simple operation such as adjustment of pH, the hydroxyapatite is changed to a gel form or a sol form so that the magnetic particles can capture the target substance, or the target substance can be eluted or alienated.

A fourteenth aspect of the present invention is characterized by comprising: the concentration device described in any one of the first to the thirteenth aspects; a shift device capable of shifting the concentration device itself and/or a container mounted outside of the concentration device; and a control device for controlling the operation of the liquid drive device, the magnetic force device and/or the shift device. As a result, the concentration processing can be automated collectively.

A fifteenth aspect of the present invention is characterized in that in the fourteenth aspect, the container has two tanks into which the suction port of the liquid passage and the discharge port of the liquid passage are respectively inserted, a thickness of a partition section for separating the two tanks being formed thinner than a distance between the suction port and the discharge port, and a bottom portion of each liquid receiving section has a slope of downward inclination toward the partition section. As a result, a large volume of liquid can be sucked completely and discharged. Hence, concentration can be performed quickly and efficiently.

A sixteenth aspect of the present invention is characterized in that in the fourteenth aspect, the control device controls so as to suck from a container storing a first volume of suspension, in which the magnetic particles having directly or indirectly captured the target substance are suspended, and pass the suspension through the liquid passage, with the magnetic force device exerting a magnetic field from outside to the liquid passage, to thereby attract the magnetic particles to the inner wall of the liquid passage and separate the magnetic particles, and so as to insert the suction port and the discharge port into a container where a second volume of liquid is stored, the second volume being smaller than the first volume, and suck and discharge the second volume of liquid to effect re-suspension to thereby concentrate the suspension containing the target substance such as bacteria suspended therein, without exerting the magnetic field by the magnetic force device.

Here, the above separation is continued until all the suspension to be sucked by the liquid passage has been sucked. When there is no more suspension to be sucked, by sucking the discharged liquid by the liquid passage, separation can be further performed. In this manner, by repeating separation, separation of magnetic particles can be performed more reliably.

A seventeenth aspect of the present invention is characterized by comprising: a capture step for capturing a target substance such as bacteria in a suspension directly or indirectly by magnetic particles; a separation step for separating the magnetic particles by exerting a magnetic field from outside of a liquid passage to the inside of the liquid passage to thereby attract the magnetic particles to an inner wall of the passage, at a time of passing a suspension having a first volume and in which the magnetic particles which have captured the target substance are suspended, through the liquid passage; a re-suspension step for re-suspending the magnetic particles which have captured the target substance in the liquid, by passing a liquid having a second volume smaller than the first volume through the liquid passage in with the magnetic particles which have captured the target substance have been separated, in the state with the magnetic field not exerted on the liquid passage; and an elution step for eluting the target substance from the magnetic particles which have captured the target substance suspended in the liquid, and separating only the magnetic particles to obtain a suspension in which the target substance is concentrated.

Here, the elution step for obtaining the suspension in which only the target substance is concentrated is performed by, for example, physical processing such as suspension and stirring, or by chemical processing involving mixing a predetermined reagent or the like.

An eighteenth aspect of the present invention is characterized in that in the seventeenth aspect, the separation step effects separation by sucking the suspension from a container storing a first volume of suspension, in which the magnetic particles having directly or indirectly captured the target substance are suspended, and passing the suspension through the liquid passage, with the magnetic field exerted from outside of the liquid passage, to thereby attract the magnetic particles to the inner wall of each liquid passage. Moreover, the re-suspension step effects re-suspension by sucking and discharging a second volume of liquid to the container where the second volume of liquid is stored, the second volume being smaller than the first volume, without exerting the magnetic field by the magnetic force device.

A nineteenth aspect of the present invention is characterized in that in either one of the seventeenth aspect or the eighteenth aspect, the separation step effects separation by sucking the suspension from a container storing a first volume of suspension in which the magnetic particles which have captured the target substance are suspended, to a storage section via the liquid suction passage, with the magnetic field exerted from outside to the liquid suction passage and the liquid discharge passage by the magnetic force device, and discharging the suspension from the storage section via the liquid discharge passage, to thereby attract the magnetic particles to the inner wall of each liquid passage. Moreover, the re-suspension step effects re-suspension by inserting the liquid suction passage and the liquid discharge passage into a container where the second volume of liquid is stored, the second volume being smaller than the first volume and substantially the same amount as that of the storage section, to thereby suck and discharge the second volume of liquid, without exerting the magnetic field by the magnetic force device.

The reason why the second volume of liquid is "smaller than the first volume and substantially the same amount as that of the storage section" is that if a liquid amount is used which is sufficient for filling the storage section, being the maximum amount of liquid which can be added to the separated magnetic particles with one suction or one discharge by the apparatus, in order to efficiently and reliably re-suspend the magnetic particles attracted to the inner wall of each liquid passage of the concentration device and separated, the magnetic particles can be most efficiently stripped off from the inner wall to effect the re-suspension.

A twentieth aspect of the present invention is characterized in that in any one of the seventeenth aspect to the nineteenth aspect, in a container storing the suspension re-suspended in the re-suspension step, the magnetic particles in the suspension are separated and then re-suspended in a liquid having a third volume smaller than the second volume, by sucking and discharging the suspension, with a magnetic field exerted on the liquid passage, by means of a pipette apparatus having a liquid passage in which liquid can pass through both in the suction direction and the discharge direction of the liquid, and a storage section communicated with the passage and having a capacity smaller than the second volume, and also having a magnetic force device for exerting and removing a magnetic field to/from the liquid passage from outside of the liquid passage.

A twenty-first aspect of the present invention is characterized in that in any one of the seventeenth aspect to the twentieth aspect, the separation step shifts all of the liquid stored in a second container to a first container, after having shifted all of the suspension stored in the first container to the second container, by sucking the liquid stored in the second container via the liquid passage, and discharging the liquid to the first container via the liquid passage, with a magnetic field exerted on the liquid passage from outside.

A twenty-second aspect of the present invention is characterized in that in any one of the seventeenth aspect to the twenty-first aspect, the separation step shifts all of the liquid stored in a second container to a first container, after having shifted all of the suspension stored in the first container to the second container, by sucking the liquid stored in the second container via the liquid suction passage, and discharging the liquid to the first container via the liquid discharge passage, with a magnetic field exerted on the liquid suction passage and the liquid discharge passage from outside. As a result, magnetic particles remaining in the suspension can be separated completely. Moreover, when all of the liquid is shifted to the first container, the process can be repeated according to the eighteenth aspect.

According to the sixteenth to the twenty-second aspects, at the time of repeating a simple operation such as passing a large volume of suspension through the liquid passage, or sucking the suspension from the liquid suction passage and discharging the suspension from the liquid discharge passage with respect to all of the suspension, since the magnetic particles in the suspension are automatically separated, all of the magnetic particles in the suspension can be efficiently and easily separated completely with a simple construction.

According to the present invention, concentration can be performed to an optional proportion, by re-suspending the separated magnetic particles in an optional volume of liquid. Therefore, as pre-stage processing of a culture process of bacteria or the like, or of an amplification process of DNA or the like, the density of a large volume of suspension containing an target substance suspended therein in a dilute amount can be increased efficiently or within a short period of time.

Since contact between the suspension containing the target substance such as bacteria suspended therein and the mechanical parts can be avoided or made minimal, the present invention is suitable for handling microorganisms such as bacteria and biopolymers such as DNA substances. Moreover, in the case where the target substance is indirectly captured by the magnetic particles via a carrier, it is not necessary to perform processing such as coating with respect to the magnetic particles, thereby enabling low-cost processing.

BEST MODE FOR CARRYING OUT THE INVENTION

Figure 1:
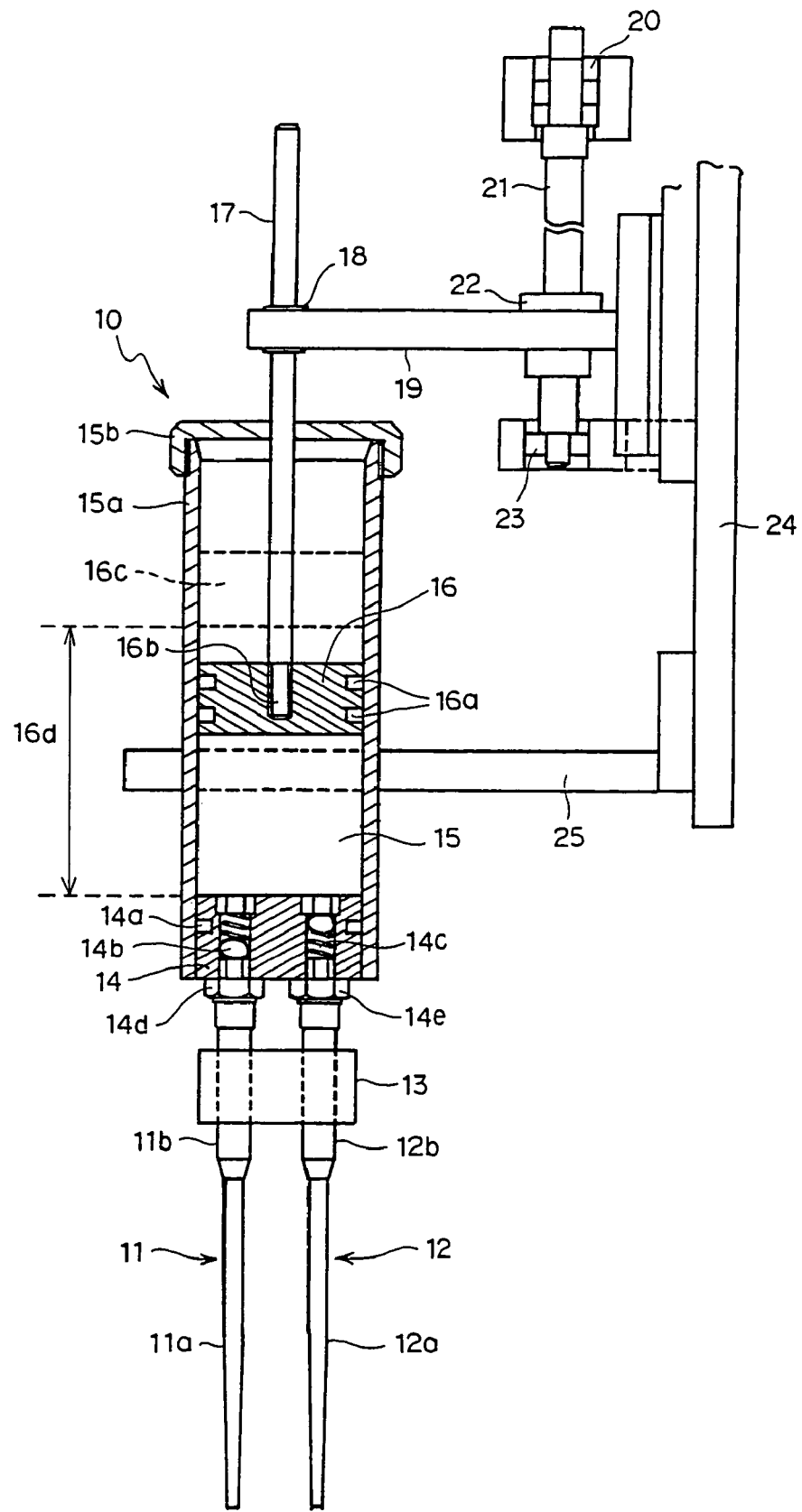
FIG. 1 shows a concentration device according to a first embodiment of the present invention.

Embodiments of the concentration device using magnetic particles according to the present invention will now be described based on the drawings. The present invention is not limited to these embodiments, unless otherwise specified. A concentration device 10 according to a first embodiment will be described with reference to FIG. 1.

The concentration device 10 comprises a liquid suction passage 11 formed substantially in a cylindrical shape, and capable of flowing liquid only in the suction direction, and a liquid discharge passage 12 formed substantially in a cylindrical shape, and capable of flowing liquid only in the discharge direction, provided so as to protrude downwards in parallel to each other.

The liquid suction passage 11 and the liquid discharge passage 12 are formed of polypropylene or the like. Each liquid passage 11, 12 is formed with a small-diameter tip portion 11a, 12a and a relatively large-diameter separation region 11b, 12b, respectively. The size of each diameter is such that, for example, the small diameter is of an order of from 2 to 3 mm, and the large diameter is of an order of about 5 mm. The length of each liquid passage 11, 12 is, for example, of an order of about 10 cm. Outside of the separation regions 11b, 12b, there is provided a magnetic force device 13 for exerting a magnetic field into the liquid passages 11b, 12b, having a sufficient size capable of attracting the magnetic particles in the suspension passing through the liquid passages 11, 12 to the inner wall thereof and separating the magnetic particles, and removing the magnetic field therefrom. As the magnetic force device 13, for example, a permanent magnet may be provided so as to be able to be brought near or be alienated from the liquid passages 11, 12, along the direction parallel to the liquid passages 11, 12 and the direction orthogonal to the protruding direction of the liquid passages 11, 12, or an electromagnet may be provided outside of the liquid passages 11, 12, to generate a magnetic field or remove the magnetic field. Alternatively, a magnetic substance may be provided so that the magnetic substance can be magnetized or demagnetized.

Each liquid passage 11, 12 is communicated with a storage section 15 via a connecting section 14. The connecting section 14 is fitted to the bottom part of a cylindrical housing 15a forming the storage section 15 and secured to the housing 15a by screwing or the like. The connecting section 14 has two through holes formed in the vertical direction, and a check valve 14b for enabling passage of liquid only in the suction direction and a check valve 14c for enabling passage of liquid only in the discharge direction are provided in the through holes. A groove for an O-ring is formed around the circumference of the connecting section 14 coming in contact with the housing 15a, and an O-ring 14a is inserted therein. The lower end of the connecting section 14 is provided with nozzles 14d, 14e into which the liquid suction passage 11 and the liquid discharge passage 12 can be inserted.

A plunger 16, serving as the pressure adjustment device, is slidably provided in the storage section 15 enclosed by the connecting section 14 and the housing 15a thereof.

Around the circumference of the plunger 16, for example, two grooves are formed, and O-rings 16a are inserted into the grooves. The plunger 16 can reciprocate, for example, between a top dead center 16c as shown in the figure and a bottom dead center at the upper end of the connecting section 14 (stroke 16d).

The mechanism for driving the plunger 16 comprises: a stepping motor 20 capable of reciprocal rotation through a predetermined angle and at a predetermined speed in accordance with instructions; a rotation shaft 21 rotated by the stepping motor 20; a bearing 23 for pivotally supporting the rotation shaft 21; a transfer drive section 22 secured to the rotation shaft 21 with an outer peripheral face formed as a pulley or the like; a ball screw 17 secured in a hole 16b formed in the vicinity of the center of the plunger 16 and provided so as to protrude in the upwards direction; a ball screw drive section 18 supported so as to be able to rotate, with an inner peripheral face screwed together with the ball screw 17 and an outer peripheral face formed as a pulley or the like; an arm-shaped member 19 having a transfer-mechanism such as a timing belt or a chain spanned between the ball screw drive section 18 and the transfer mechanism 22, pivotally supporting the transfer mechanism and the ball screw drive section 18 and secured to a support member 24; and a fixed member 25 fixing the housing 15a and fixed to the support member 24.

Moreover, the concentration device 10 comprises a shift section (not shown) which makes it possible to shift from/to a container, as a whole. As the shift section, there is a case where the concentration device 10 can be moved, a case where only a container can be moved, or a case where both of a dispensing device and the container can be moved.

In this embodiment, a shift section (not shown) for shifting a stage on which the concentration device 10 itself and the container are placed is provided. Moreover, there are provided a stepping motor 20 provided in the pressure adjustment device of the concentration device 10, a computer serving as a control device for controlling the magnetic field of the magnetic force device 13, a display section such as CRT, a keyboard, a mouse, an input section of a reader for reading a recording medium on which a program and data are stored, such as a floppy disk, a CD or an MD, and an information processing unit (not shown) having a communication section for connecting to the Internet or the like.

Figure 2:
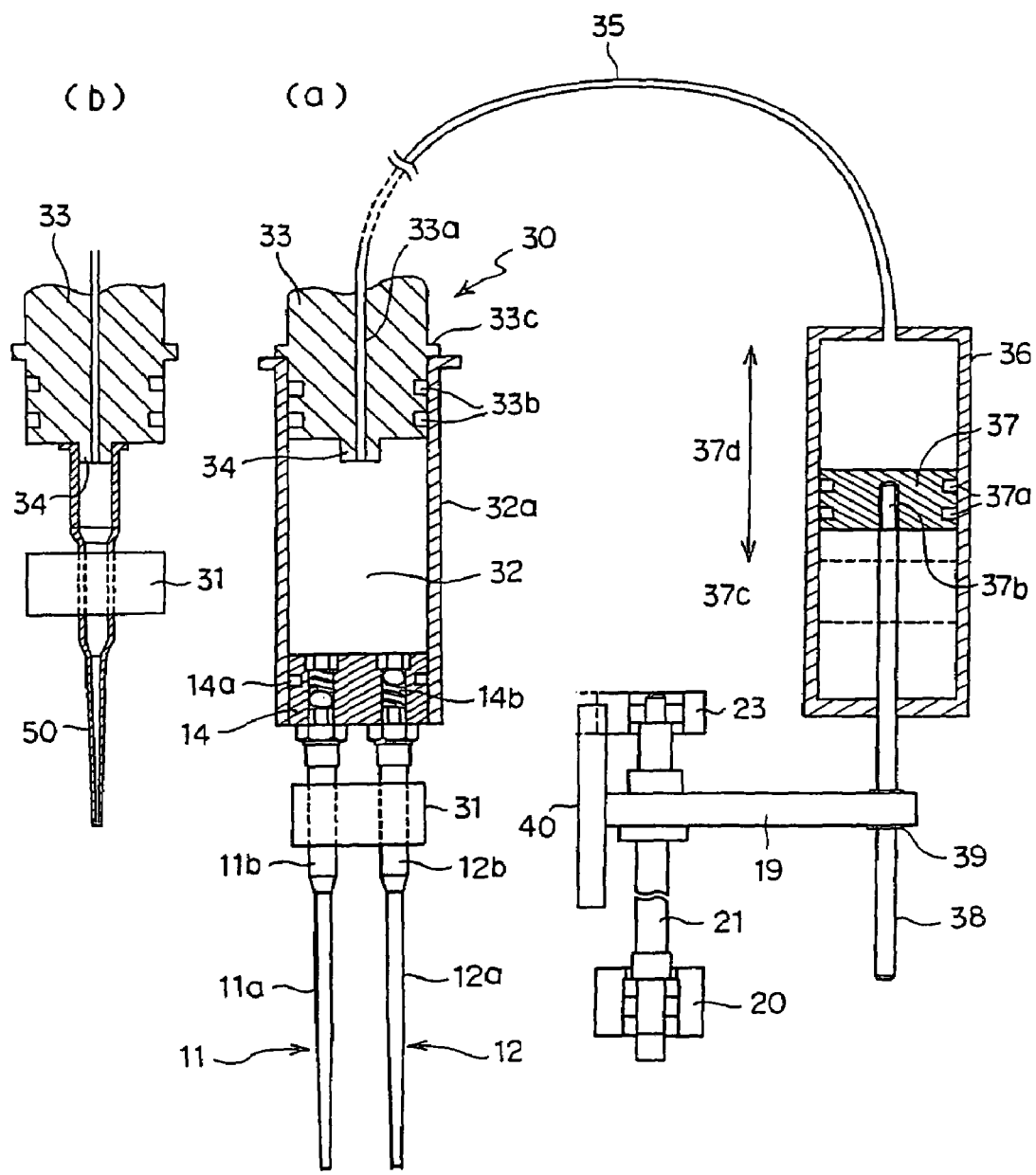
FIG. 2 shows a concentration device according to a second embodiment of the present invention.

FIG. 2 shows a concentration device 30 according to a second embodiment. Since the reference symbols the same as those of FIG. 1 denote the same members, description thereof is omitted. As shown in FIG. 2(a), the concentration device 30 according to the second embodiment comprises a liquid suction passage 11 and a liquid discharge passage 12 provided so as to protrude downwards in parallel to each other, as in the concentration device 10 according to the first embodiment.

Moreover, outside of the separation regions 11b, 12b of the respective liquid passages 11, 12, there is provided a magnetic force device 31 for generating or removing a magnetic field capable of exerting a magnetic field on each liquid passage 11b, 12b and attracting the magnetic particles in the suspension passing through the liquid passages 11, 12 to the inner wall of the liquid passages 11, 12 and separating the magnetic particles, and which can move in the vertical direction. As the magnetic force device 31, for example, a permanent magnet may be provided so as to be able to be brought near to or be alienated from the liquid passages 11, 12, along the direction parallel to the liquid passages 11, 12 and the direction orthogonal to the protruding direction of the liquid passages 11, 12, or an electromagnet may be provided, to generate or remove a magnetic field. Alternatively, a magnetic substance may be provided such that the magnetic substance can be magnetized or demagnetized.

The respective liquid passages 11, 12 are communicated with a storage section 32 via a connecting section 14. The storage section 32 has a cylindrical housing 32a, and at the bottom portion thereof, has the connecting section 14 fitted to the housing 32a and secured thereto by screwing or the like, and at the upper end thereof, a stopper section 33 is fitted by screwing or the like and secured detachably. At the bottom center of the stopper section 33, there is provided a columnar convex portion 34 so as to protrude downwards. Along the central axis of the stopper section 33 and the convex portion 34, a through hole 33a is provided, and grooves 33b are formed around the circumference of the stopper section 33, at a portion where the stopper section 33 is brought into contact with the housing 32a, and O-rings are inserted therein. An annular flange 33c is provided around the circumference of the stopper section 33 to stop further insertion of the stopper section 33 in the housing 32a, thereby enabling positioning in the storage section 32.

The storage section 32 is communicated with a pump 36, serving as the pressure adjustment device, via the through hole 33a and a vent pipe 35. Gas is sucked into the storage section 32 and gas is exhausted from the storage section 32 by the pump 36. The pump 36 has a plunger 37, and is capable of vertical movement between a top dead center position and a bottom dead center position 37c (stroke 37d). Grooves 37a are formed around the circumference of the plunger 37, and O-rings are inserted in the grooves 37a. There are also provided a ball screw 38 secured to a hole 37b formed in the vicinity of the center of the plunger 37 and provided so as to protrude downwards, and a ball screw drive section 39 supported so as to be able to rotate, with the inner peripheral face screwed together with the ball screw 38 and the outer peripheral face formed as a pulley or the like.

In the concentration device 30 according to this embodiment, the liquid suction passage 11, the liquid discharge passage 12, the connecting section 14 and the storage section 32 are provided detachably with respect to the stopper section 33. In the case where the storage section 32 or the like is detached from the stopper section 33, as shown in FIG. 2(b), a pipette tip 50 can be attached to the protruding portion 34. The pipette tip 50 has a large-diameter storage section attached to the protruding portion 34 at the upper portion thereof, and a small-diameter liquid passage communicated with the storage section and having a smaller diameter than that of the storage section. The liquid passage further has a separation region for separating the magnetic particles by attracting the magnetic particles to the inner wall thereof with the magnetic field exerted therein, and a tip portion having a smaller diameter than that of the separation region. In the case where the pipette tip 50 is attached, the magnetic force device 31 is moved to the position of the separation region of the pipette tip 50 so that the magnetic field can be reliably exerted on the separation region.

Figure 3:
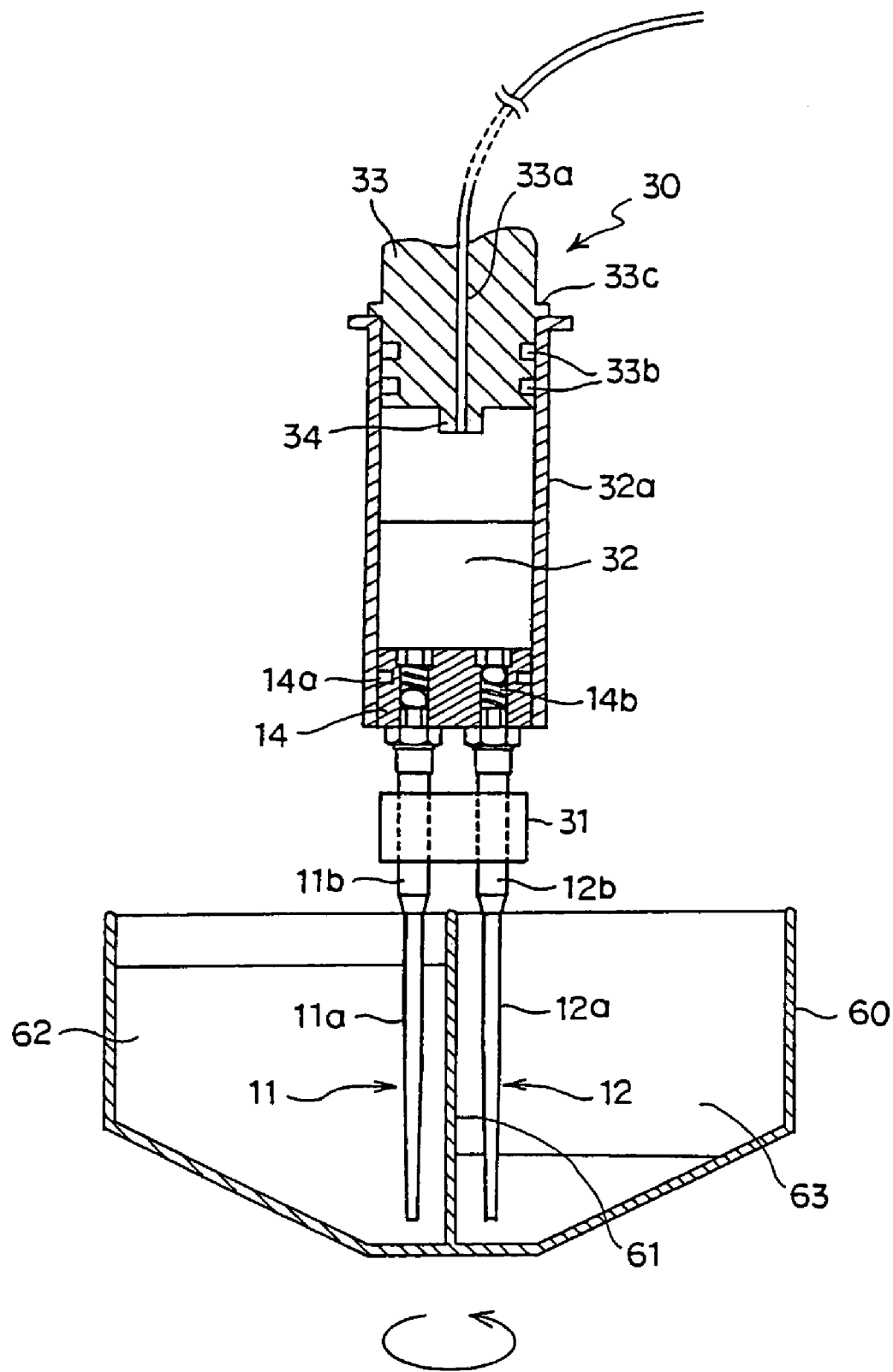
FIG. 3 shows a concentration device according to a third embodiment of the present invention.

A concentration method for a suspension of bacteria or the like according to a third embodiment will now be described, with reference to FIG. 3. This method uses the above concentration device 30, as well as a first container 60 having two concentration tanks 62, 63, into which the liquid suction passage 11 and the liquid discharge passage 12 are respectively inserted, and a normal second container.

The first container 60 for concentration is a container constructed such that the thickness of a partition 61 for partitioning two tanks 62, 63 is formed thinner than the distance between the liquid suction passage 11 and the liquid discharge passage 12, and the bottom portion of each tank 62, 63 has a slope having a downward gradient towards the partition 61.

In the case where a suspension of bacteria or the like is concentrated, a large amount of suspension containing magnetic particles suspended therein, which have directly or indirectly captured bacteria or the like, being the target substance, is stored beforehand in the one tank 62 of the container 60 for concentration. Also, an aqueous solution is stored in the normal container, in which a necessary reagent is dissolved in water in an amount as large as that of the storage section 32 of the concentration device 30.

In order to capture the bacteria indirectly by the magnetic particles, a minute carrier of a gel substance such as hydroxyapatite, bacteria being the target substance, and α-magnetic particles without coating are mixed or suspended in a liquid. As a result, the above-described minute carrier of a gel substance takes the bacteria and the α-magnetic particles thereinto, to thereby have the α-magnetic particles capture the target substance such as bacteria indirectly. In order to capture bacteria or the like directly by the magnetic particles, β-magnetic particles coated with a substance capable of being bonded with bacteria or the like are used as the magnetic particles.

In step S1, an operator gives an instruction to, for example, the above described information processing unit, to move the concentration device 30 vertically or horizontally to thereby insert the liquid suction passage 11 of the concentration device 30 into the tank 62 in which a large amount of suspension is stored, of the container 60 for concentration, and the liquid discharge passage 12 into the vacant tank 63 of the container 60 for concentration. Then, the operator brings the permanent magnet or electromagnet of the magnetic force device 13 near each liquid passage 11, 12 from outside of each liquid passage 11, 12, to thereby exert a magnetic field into the liquid passage 11, 12. By moving the plunger 37 from the top dead center downwards, with the magnetic field exerted, the suspension is sucked to the storage section 32 via the liquid suction passage 11, with an air layer therebetween.

As for the drive of the plunger 37, by the rotation driving of the stepping motor 20, the rotation of the drive section 22 secured to the rotating rotation shaft 21 makes the ball screw drive section 39 rotate via the transfer mechanism. By the rotation of the ball screw drive section 39, the ball screw 38 threaded with the ball screw drive section 39 is translationally moved downwards, without rotating. By this translational motion of the ball screw 38, the plunger 37 moves downwards, to thereby suck the suspension from the liquid suction passage 11 to the storage section 32. When the suspension is sucked to the storage section 32, the plunger 37 is moved from the bottom dead center to the top dead center. The liquid sucked to the storage section 32 is then discharged to the other vacant tank 63 of the first container 60 for concentration, via the liquid discharge passage 12.

In this manner, at the time when the suspension passes through each liquid passage 11, 12, the α-magnetic particles which have captured the target substance contained in the suspension via the carrier are attracted to the inner wall of each liquid passage 11, 12 and separated. This suction and discharge are performed until all of the suspension in one tank 62 is transferred to the other tank. After the transfer has been completed, the concentration device 30 is moved upwards, and the container 60 is rotated by 180° or the concentration device 30 is rotated by 180°, and thereafter, the concentration device 30 is again moved downwards, to thereby insert the liquid suction passage 11 into the tank 63 where the transferred suspension is stored and insert the liquid discharge passage 12 into the vacant tank 62. At that time, the above step may be repeated more than once, while attracting the already separated α-magnetic particles to the liquid passage. Thereby, the α-magnetic particles in the suspension can be more reliably separated.

In step S2, the concentration device 30 is moved upwards, to pull out each liquid passage 11, 12 from the first container 60, while keeping the separated magnetic particles attracted to the concentration device 30. Thereafter, the concentration device 30 itself or a stage on which the container is mounted is moved horizontally, to thereby position the second container (not shown) below the concentration device 30. By moving the concentration device 30 downwards, both of the liquid passages 11, 12 are inserted into the second container. Then, the permanent magnet or the electromagnet of the magnetic force device 31 of the concentration device 30 is alienated from the liquid passages 11, 12, and in the case of the electromagnet, the electric current is cut off. Suction and discharge of liquid from the second container is then repeated with the magnetic field removed, so that the separated magnetic particles are re-suspended in the liquid.

Next, the storage section 32 attached to the stopper section 33 provided in the pressure adjustment device is detached, and the pipette tip 50 is attached to the protruding portion 34 of the stopper section 33, thereinstead. Also, the magnetic force device 31 is moved so as to be positioned in the separation region of the pipette tip 50. By repeating suction and discharge of the suspension stored in the second container, with the magnetic field exerted on the separation region of the pipette tip 50, the α-magnetic particles which have captured the target substance via the carrier are attracted to the pipette tip 50 and separated. The storage section of the pipette tip 50 has a smaller capacity than that of the storage section 32 of the concentration device 30. Therefore this operation is performed by repeating suction and discharge in a volume that the pipette tip 50 can suck.

The pipette tip 50 is moved upwards, while keeping the separated magnetic particles attracted to the pipette tip 50, and the device itself having the pipette tip 50 attached thereto or the container is moved, to thereby position a third container storing liquid in an amount of 1 to 2 cc below the pipette tip 50. Then, with the magnetic field removed by the magnetic force device 31, suspension or stirring is performed by suction and discharge with respect to the pipette tip 50, to thereby elute or alienate the target substance from the α-magnetic particles and the carrier having captured the target substance. In order to perform elution or alienation, the target substance is eluted or alienated, by forming the hydroxyapatite in a sol form or dissolving it by using an aqueous solution whose pH is adjusted, in the case of the carrier being hydroxyapatite, or by physical processing such as stirring, in the case of the carrier being a cellulose carrier. Next, a magnetic field is exerted on the separation region of the pipette tip 50 by the magnetic force device 31 and the suspension is sucked and discharged to thereby attract only the α-magnetic particles to the separation region and separate these, and the separated α-magnetic particles are removed. As a result, the concentrated suspension containing the target substance suspended therein can be obtained.

By using the concentrate containing the target substance suspended therein obtained in this manner, various processing can be performed.

In the case where the target substance is a Vero toxin (VT) gene of Vero toxin producing *E. coli* (VTEC) represented by O157:H7, a description is given below of a case where the obtained suspension of the gene is subjected to amplification processing.

The pipette tip 50 of the concentration device 30 is detached, and a new pipette tip is attached. Also, in order to capture the Vero toxin gene, antibody coated magnetic particles (β-magnetic particles) are used.

Figure 4:
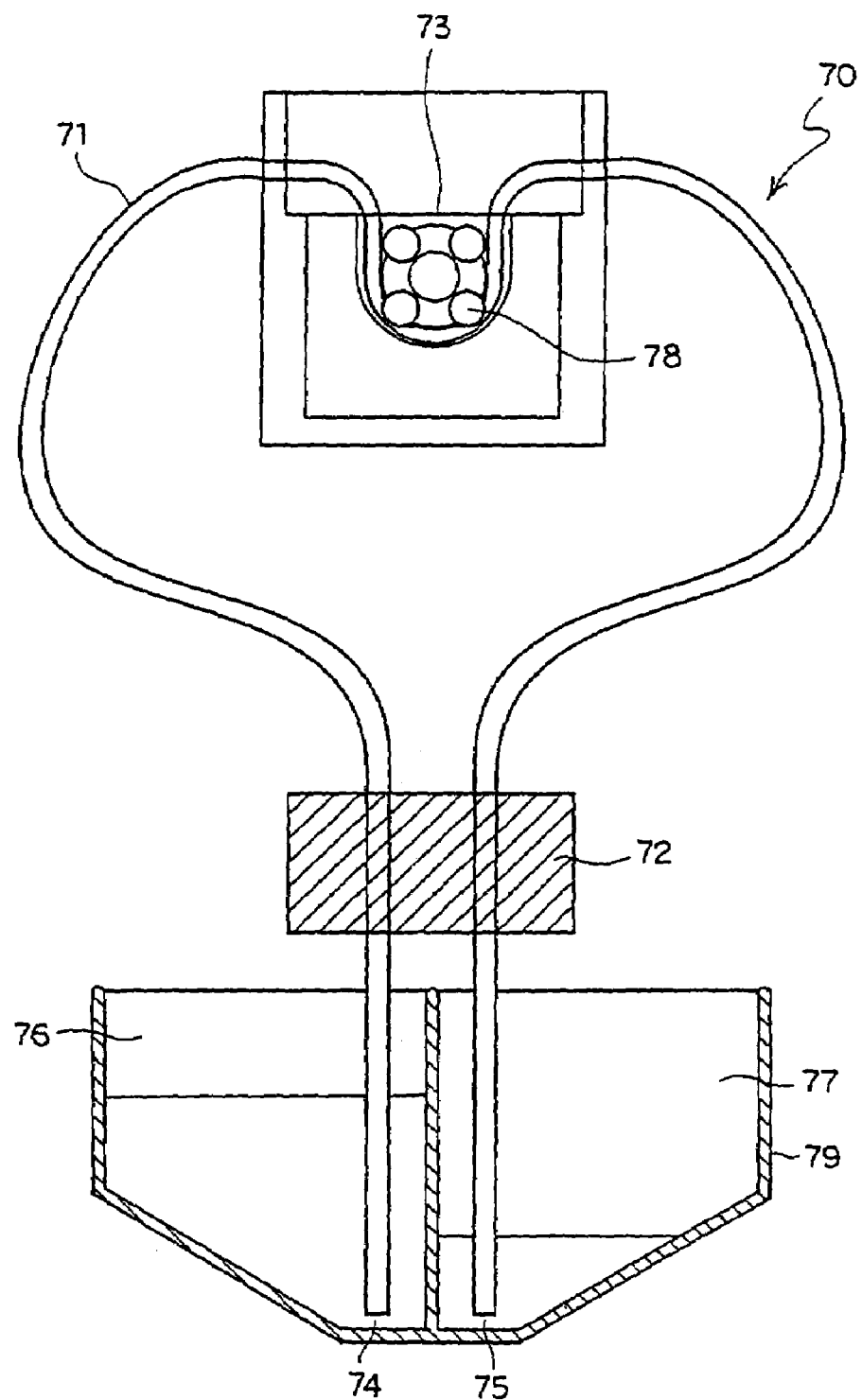
FIG. 4 shows a concentration device according to a fourth embodiment of the present invention.

A concentration device 70 according to a fourth embodiment will now be described with reference to FIG. 4.

The concentration device 70 according to the fourth embodiment comprises: a liquid passage 71 formed of a resilient body, having a suction port 74 and a discharge port 75, in which liquid passes therethrough; a magnetic force device 72 capable of exerting a magnetic field into the liquid passage, which can separate magnetic particles which have captured directly or indirectly the target substance suspended in the liquid, by attracting the magnetic particles to the inner wall of the liquid passage from outside of the liquid passage 71; and a peristaltic pump 73 for driving so that liquid passes through the liquid passage 71.

The concentration device 70 uses a tank 76 for storing a suspension having captured the target substance therein, into which a suction port 74 is inserted, and a different tank 77 into which a discharge port 75 is inserted.

The above peristaltic pump 73 is for transferring liquid, while sequentially pressing the liquid passage 71 formed of a resilient body along the transfer direction of the liquid by a rotation pressing portion 78 from outside, and collapsing and contracting the liquid passage 71 in the transfer direction of the liquid.

When the peristaltic pump 73 is driven, the rotation pressing body advances the liquid passage 71 formed of a resilient body while collapsing it, to thereby pass the liquid therethrough from the suction port to the discharge port. At that time, the magnetic particles contained in the suspension are attracted to the inner face of the liquid passage 71 at a predetermined position, due to an influence of a magnetic field of the magnetic force device 72 and separated.

In the middle of the liquid passage 71, a switchover mechanism for switching over the liquid passage, for re-suspending and discharging the separated magnetic particles may be provided. Moreover, the liquid passage 71 may be provided so that when the magnetic particles are attracted and separated, the whole or a part can be taken out from the mechanical portion such as at the pump 73. According to this embodiment, since the mechanism for passing the liquid through the liquid passage, and the liquid, do not come in contact with each other, the mechanism is not contaminated by the liquid. Hence reuse is possible by merely replacing the liquid passage, thereby enabling reliable separation and concentration. Furthermore, since only the liquid passage can be taken out and used for further processing, unnecessary connection can be avoided, thereby making the processing quick and simple.

The above embodiments have been described for better understanding of the present invention, and in no way limit other embodiments. Therefore, the present invention can be modified within the scope of the present invention. For example, in the above description, the pressure adjustment device is a piston or a piston-type pump, but the pressure adjustment device is not limited thereto, and a centrifugal pump may be used. Also, it has been described that the piston is driven by a ball screw mechanism, but it is not limited to this case, and it may be driven by a cam mechanism or a link mechanism. Moreover, the size, material or structure of the parts described in the embodiments and the kinds of reagents used are not limited thereto.

What is claimed is:

1. A concentration method using magnetic particles comprising:

capturing a target substance in a first suspension having a first volume directly or indirectly with magnetic particles;

separating the magnetic particles from the first suspension by sucking the first suspension from a first container storing the first suspension, passing the first suspension through a first liquid passage, and exerting a magnetic field from outside the first liquid passage to the inside of the first liquid passage to thereby attract the magnetic particles to an inner wall of the first liquid passage;

suspending the magnetic particles in a liquid having a second volume to obtain a second suspension, wherein the second volume is less than the first volume, by sucking the liquid from a second container storing the liquid, passing the liquid through the first liquid passage without exerting a magnetic field on the first liquid passage and discharging the second suspension into the second container; and eluting the target substance from the magnetic particles in the second suspension.

2. A concentration method using magnetic particles according to claim 1 further comprising, concentrating the magnetic particles in the second suspension, by sucking the second suspension from the second container, passing the second suspension through a second liquid passage having a suction/discharge portion and a storage portion wherein liquid can pass in a suction direction and a discharge direction through the suction/discharge portion and the storage portion has a capacity smaller than the second volume and discharging the second suspension into a third container while a magnetic field is exerted on the second liquid passage.

3. A concentration method using magnetic particles comprising:

capturing a target substance in a first suspension having a first volume directly or indirectly with magnetic particles;

separating the magnetic particles from the first suspension by passing the first suspension through a first liquid passage having a suction portion, a storage portion and a discharge portion and exerting a magnetic field from outside the first liquid passage to the inside of the first liquid passage to thereby attract the magnetic particles to an inner wall of the first liquid passage;

suspending the magnetic particles in a liquid having a second volume to obtain a second suspension, wherein the second volume is less than the first volume, by passing the liquid through the first liquid passage without exerting a magnetic field on the first liquid passage; and eluting the target substance from the magnetic particles in the second suspension;

wherein the first suspension is stored in a first container and is passed through the first liquid passage by sucking the first suspension from the first container into the storage portion of the first liquid passage while exerting the magnetic field from outside the first liquid passage, and discharging the first suspension from the storage section through the discharge portion of the first liquid passage;
wherein the liquid having a second volume is stored in a second container, the second volume being substantially the same as the volume of the storage section of the first liquid passage; and
wherein the liquid is passed through the first liquid passage by sucking the liquid from the second container into the storage section of the first liquid passage without exerting a magnetic field on the first liquid passage, and discharging the liquid into the second container.

4. A concentration method using magnetic particles according to claim 3 further comprising, concentrating the magnetic particles in the second suspension, by sucking the second suspension from the second container, passing the second suspension through a second liquid passage having a suction/discharge portion and a storage portion wherein liquid can pass in a suction direction and a discharge direction through the suction/discharge portion and the storage portion has a capacity smaller than the second volume and discharging the second suspension into a third container while a magnetic field is exerted on the second liquid passage.

* * * * *